US00PP19535P3

(12) United States Plant Patent
van Kleinwee

(10) Patent No.: US PP19,535 P3
(45) Date of Patent: Dec. 2, 2008

(54) ***GERANIUM* PLANT NAMED 'ZODAROWIE'**

(50) Latin Name: *Pelargonium zonale (L.) L'Hérit. ex Ait*
Varietal Denomination: Zodarowie

(75) Inventor: Theodorus Cornelis Maria van Kleinwee, Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 10 days.

(21) Appl. No.: 11/633,379

(22) Filed: Dec. 4, 2006

(65) Prior Publication Data

US 2008/0134392 P1 Jun. 5, 2008

(51) Int. Cl.
*A01H 5/00* (2006.01)

(52) U.S. Cl. ..... Plt./325
(58) Field of Classification Search ..... Plt./325
See application file for complete search history.

(56) References Cited

PUBLICATIONS

UPOVROM search for cultivar Zodarowie PBR 20051199. p. 1.*

* cited by examiner

*Primary Examiner*—Annette H Para
(74) *Attorney, Agent, or Firm*—S. Matthew Edwards

(57) ABSTRACT

A new *Geranium* plant, particularly distinguished by the lavender pink flower color with blotch, strong vigor, green foliage with strong zone, and round plant structure with medium strong branching.

1 Drawing Sheet

Latin name of the genus and species of the plant claimed: *Pelargonium zonale* (*L.*) *L'Hérit. ex Ait.*
Varietal denomination: 'Zodarowie'.

BACKGROUND OF THE NEW PLANT

The present invention comprises a new *Geranium*, botanically known as *Pelargonium zonale* (*L.*) *L'Hérit ex Ait,* and hereinafter referred to by the variety name 'Zodarowie.'

'Zodarowie' is a product of a planned breeding program. The new cultivar 'Zodarowie' has large, semi-double flowers, is relatively vigorous, but with a well-branched growth habit, and has good heat resistance.

'Zodarowie' originates from a hybridization in a controlled breeding program in Enkhuizen, The Netherlands. The female parent was an unpatented hybrid seedling identified as no. 1076 with lavender color with nice flower shape, floriferous, and big umbels. The male parent of 'Zodarowie' was an unpatented hybrid unknown seedling with unknown characteristics.

'Zodarowie' was selected as one flowering plant within the progeny of the stated cross in 2001 in a controlled environment in Enkhuizen, The Netherlands.

The first act of asexual reproduction of 'Zodarowie' was accomplished when vegetative cuttings were from the initial selection in the Fall of 2001 in a controlled environment in Enkhuizen, the Netherlands.

Horticultural examination of plants grown from cuttings of the plant initiated in April of 2002 in Enkhuizen, The Netherlands, and continuing thereafter, has demonstrated that the combination of characteristics as herein disclosed for 'Zodarowie' are firmly fixed and are retained through successive generations of asexual reproduction.

'Zodarowie' has not been observed under all possible environmental conditions. The phenotype may vary significantly with variations in environment such as temperature, light intensity and day length.

BRIEF DESCRIPTION OF THE NEW VARIETY

The accompanying photographic drawing shows typical flower and foliage characteristics 'Zodarowie' with colors being as true as possible with an illustration of this type. The photographic drawing shows a flowering potted plant of the new variety.

DETAILED BOTANICAL DESCRIPTION

The measurements were taken in Enkhuizen, Netherlands, in August 2005 on 26 week old plants that were growing in window boxes. Culture of these plants started mid February, 2005 in the greenhouse; plants were transferred to window boxes mid May, 2005.

BRIEF SUMMARY OF INVENTION

The following observations, measurements, and comparisons describe plants grown outside in Enkhuizen, The Netherlands. The following traits have been repeatedly observed and are determined to be basic characteristics of the new variety. The combination of these characteristics distinguishes this *Geranium* as a new and distinct variety.

Color references are primarily to the 2001 R.H.S. Colour Chart of The Royal Horticultural Society of London.

Plants of the new *Geranium* differ primarily from the plants of the female parent '1076' in the following characteristics:

The plants of the female parent '1076' have more of a lavender shade of color than plants of the New *Geranium*. The plants of the female parent '1076' also have a more cup shaped flower shape, are slightly less floriferous, and have somewhat bigger umbels than plants of the new *Geranium*.

The male parent of the new *Geranium* is an undefined seedling from a mix of pollen derived from unpatented seedlings, comprising all kinds of shades of pink colors and different kinds of other characteristics. Specific differences between the varieties are therefore unknown.

TABLE 1

DIFFERENCES BETWEEN THE NEW VARIETY 'ZODAROWIE' AND A SIMILAR VARIETY

| | 'Zodarowie' | 'Klegany' (U.S. Plant Pat. No. 9,110) |
|---|---|---|
| Flower color (upper side of upper petal) | No blotch | Blotch |
| Leaf zoning | Present, color 187A | Absent |
| Leaf color (upper side) | 137B | 146A |

Plant:
- *Plant height* (*cm*).—25.
- *Plant height* (*inflorescence included*) (*cm*).—38.
- *Plant width* (*cm*).—60.
- *Plant shape.*—Round.

Foliage:
- *Length* (*cm*).—6.
- *Width* (*cm*).—10.
- *Shape.*—Reniform.
- *Base shape.*—Cordate.
- *Base size* (*cm*).—5.
- *Apex shape.*—Very weak lobes.
- *Apex size* (*cm*).—3.
- *Color of upper surface.*—137B.
- *Color of lower surface.*—146B.
- *Color of zone.*—187A.
- *Color of veins.*—146C.
- *Margin.*—Bicrenate.
- *Petioles length* (*cm*).—6–8.
- *Diameter of petiole* (*mm*).—3.
- *Leaves smooth and hairy.*—Only at nerves.
- *Texture of leaves.*—Upper surface smooth.
- *Veins.*—Palmate.

Stem:
- *Length of internodes* (*mm*).—10–30.
- *Color of stem.*—146C.
- *Diameter* (*mm*).—10.

Inflorescence:
- *Shape.*—Round outline.
- *Diameter* (*cm*).—11.
- *Umbel depth* (*cm*).—6.
- *Length of peduncle* (*cm*).—8–15.
- *Peduncle diameter* (*mm*).—3–4.
- *Color of peduncle.*—146B little; 183B.
- *Length of pedicel* (*cm*).—2–3.5.
- *Color of pedicel.*—184A, with 146D spread over pedicel.
- *Number of flowers per inflorescence.*—35.

Corolla:
- *Form.*—Weakly semi-double type, appears almost as single type.
- *Shape.*—Round outline, upper petals about the same size as the lower petals, flat shaped.
- *Length of flower* (*cm*).—4.5.
- *Width of flower* (*cm*).—4.5.
- *Number of petals.*—5–7.
- *Length of petals* (*upper/lower*) (*mm*).—Upper 27. Lower 25.
- *Width of petals* (*upper/lower*) (*mm*).—Upper 28. Lower 20.
- *Shape petals.*—Obovate, base acute, upper end is truncate or rounded, margin is entire.
- *Color upper side of upper petals.*—N74A.
- *Color upper side of lower petals.*—N74A, base 73C.
- *Color lower side of upper petals.*—73A fading to 73D at base.
- *Color lower side of lower petals.*—73A fading to 73D at base.
- *Number of petaloids.*—0.
- *Fading color when flower starts aging.*—No.
- *Duration of flowering.*—Continuous flowering throughout the Summer.

Bud (just before opening):
- *Shape.*—Narrow elliptic.
- *Shape base of bud.*—Truncate.
- *Shape top of bud.*—Acuminate.
- *Sepals hairy and smooth.*—Yes.
- *Length* (*mm*).—10.
- *Width* (*mm*).—5.
- *Color.*—146C.
- *Number of sepals.*—5.
- *Color of sepals.*—152C.
- *Length of sepals* (*mm*).—9.
- *Width of sepals* (*mm*).—3–4.

Reproductive organs:
- *Number of lobes of stigma.*—5.
- *Color stigma.*—61B.
- *Length of style* (*mm*).—3.
- *Color of style.*—61B.
- *Number of anthers.*—7–12.
- *Length of anthers* (*mm*).—3.
- *Shape of anthers.*—*Ovate.*
- *Length filaments* (*mm*).—5.
- *Color of filaments.*—155D, Top N74B.
- *Pollen present.*—Yes.
- *Color of pollen.* —32 A.
- *Fertility/seed set.*—No.

Disease/pest resistance: No disease/pest resistance has been observed to date.

What is claimed is:

1. A new and distinct variety of *Geranium* plant substantially as illustrated and described herein.

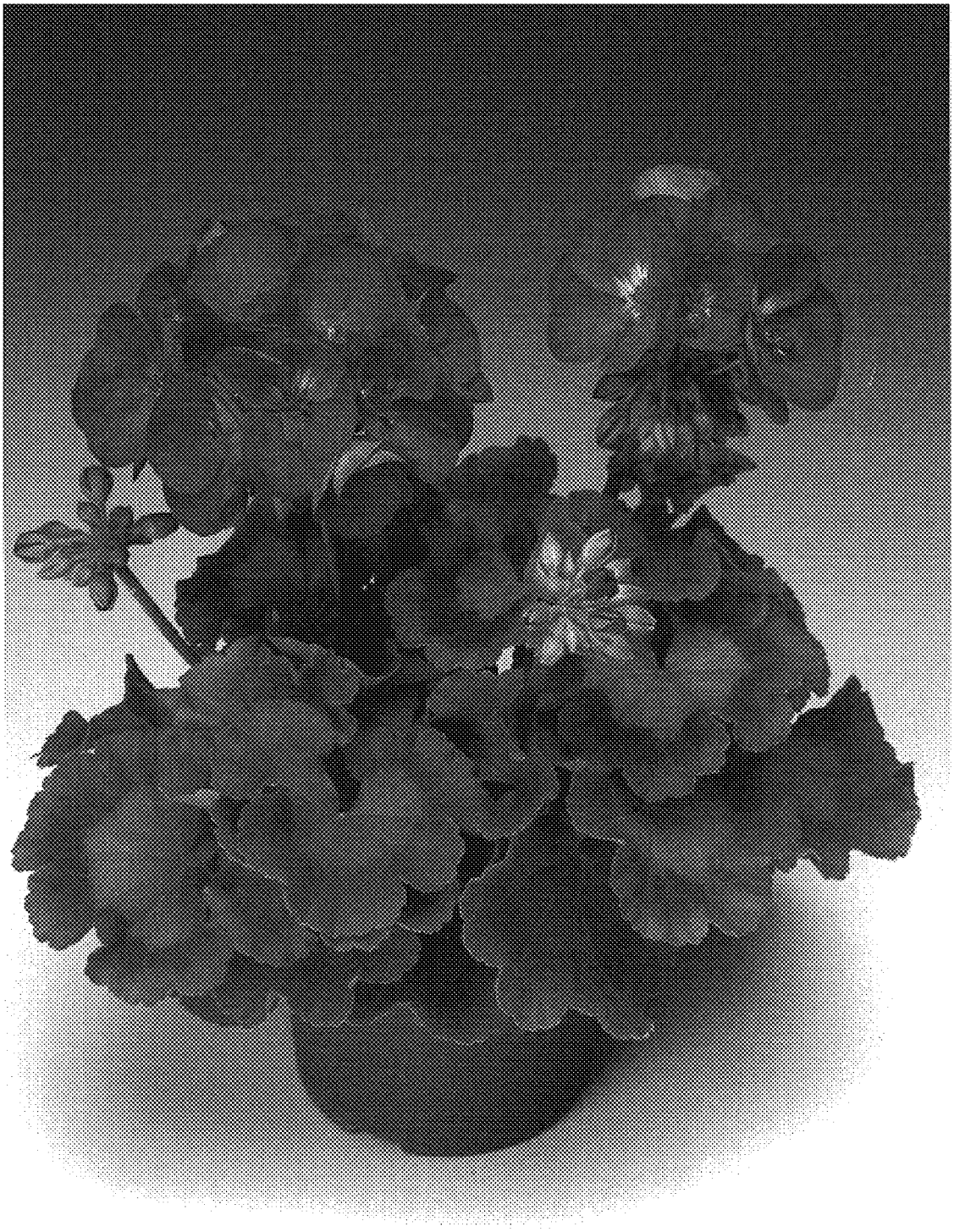

* * * * *